(12) United States Patent
Nishimura et al.

(10) Patent No.: US 10,828,480 B2
(45) Date of Patent: Nov. 10, 2020

(54) APPLICATOR (71) Applicant: HISAMITSU PHARMACEUTICAL CO., INC., Tosu (JP)

(72) Inventors: Shinpei Nishimura, Tsukuba (JP); Seiji Tokumoto, Tsukuba (JP); Masafumi Ono, Tosu (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 323 days.

(21) Appl. No.: 15/756,234

(22) PCT Filed: Aug. 19, 2016

(86) PCT No.: PCT/JP2016/074221
§ 371 (c)(1),
(2) Date: Jun. 7, 2018

(87) PCT Pub. No.: WO2017/038499
PCT Pub. Date: Mar. 9, 2017

(65) Prior Publication Data
US 2019/0083770 A1    Mar. 21, 2019

(30) Foreign Application Priority Data
Sep. 2, 2015 (JP) ................................ 2015-172793

(51) Int. Cl.
*A61M 37/00* (2006.01)

(52) U.S. Cl.
CPC . *A61M 37/0015* (2013.01); *A61M 2037/0023* (2013.01)

(58) Field of Classification Search
CPC ...... A61M 37/0015; A61M 2037/0023; A61M 2037/0061; A61M 2205/58
See application file for complete search history.

(56) References Cited

U.S. PATENT DOCUMENTS 6,334,856 B1    1/2002  Allen et al.
2002/0091357 A1*  7/2002  Trautman ............. A61B 17/205
                                                         604/117
(Continued)

FOREIGN PATENT DOCUMENTS

AU    2012201016 A1    3/2012
CA      2425312 A1    4/2002
(Continued)

OTHER PUBLICATIONS

International Search Report dated Nov. 22, 2016 corresponding to application No. PCT/JP2016/074221.
(Continued)

*Primary Examiner* — Bhisma Mehta
*Assistant Examiner* — Daniel Moore
(74) *Attorney, Agent, or Firm* — Nath, Goldberg & Meyer; Joshua B. Goldberg; Tanya E. Harkins (57) ABSTRACT An applicator according to one embodiment includes a housing having a tubular shape with one closed end, and configured to house an elastic member and a piston plate for transmitting biasing force of the elastic member to the microneedles, and release means configured to release the piston plate engaged in a manner resisting against the biasing force of the elastic member in the housing, to cause the piston plate to move toward an opening of the housing along an axial direction of the housing. The release means is configured, when the release means releases the engagement of the piston plate by moving toward the housing in the axial direction, to transmit force in a direction toward the opening to the housing.

4 Claims, 9 Drawing Sheets

(56) References Cited

U.S. PATENT DOCUMENTS

| | | |
|---|---|---|
| 2002/0123675 A1 | 9/2002 | Trautman et al. |
| 2006/0074376 A1 | 4/2006 | Kwon |
| 2008/0039805 A1 | 2/2008 | Frederickson et al. |
| 2008/0156594 A1 | 7/2008 | Kobayashi |
| 2009/0198189 A1 | 8/2009 | Simons et al. |
| 2010/0222743 A1 | 9/2010 | Frederickson et al. |
| 2011/0275994 A1 | 11/2011 | Iwase et al. |
| 2011/0276027 A1 | 11/2011 | Trautman et al. |
| 2012/0010529 A1 | 1/2012 | Chickering, III et al. |
| 2012/0130207 A1 | 5/2012 | O'Dea et al. |
| 2014/0039458 A1 | 2/2014 | Constantineau et al. |
| 2014/0128818 A1 | 5/2014 | Ogura et al. |
| 2014/0243747 A1 | 8/2014 | Tokumoto et al. |
| 2015/0314117 A1* | 11/2015 | Arami .............. A61M 37/0015 604/173 |

FOREIGN PATENT DOCUMENTS

| | | |
|---|---|---|
| CA | 2490137 A1 | 12/2003 |
| CN | 1479589 A | 3/2004 |
| CN | 101513550 A | 8/2009 |
| CN | 1027532234 A | 10/2012 |
| CN | 104245041 A | 12/2014 |
| EP | 2399643 A1 | 12/2011 |
| JP | 2004510534 A | 4/2004 |
| JP | 2005533625 A | 11/2005 |
| JP | 2006500973 A | 1/2006 |
| JP | 2006276200 A | 10/2006 |
| JP | 2007516781 A | 6/2007 |
| JP | 2008520369 A | 6/2008 |
| JP | 2008535587 A | 9/2008 |
| JP | 2010211890 A | 9/2010 |
| JP | 4659332 B2 | 3/2011 |
| JP | 2012100783 A | 5/2012 |
| JP | 2014509208 A | 4/2014 |
| KR | 101111144 B1 | 2/2012 |
| TW | 201231109 A1 | 8/2012 |
| TW | 201321037 A | 6/2013 |
| TW | 201330893 A | 8/2013 |
| WO | 0009184 A1 | 2/2000 |
| WO | 0230300 A2 | 4/2002 |
| WO | 2004009172 A1 | 1/2004 |
| WO | 2005123173 A1 | 12/2005 |
| WO | 2006055795 A1 | 5/2006 |
| WO | 2006103727 A1 | 10/2006 |
| WO | 2007124411 A1 | 11/2007 |
| WO | 2009107806 A2 | 9/2009 |
| WO | 2011075105 A1 | 6/2011 |
| WO | 2012046816 A1 | 4/2012 |
| WO | 2012088154 A1 | 6/2012 |
| WO | 2013015136 A1 | 1/2013 |
| WO | 2013051568 A1 | 4/2013 |
| WO | 2014097837 A1 | 6/2014 |
| WO | 2013015136 A1 | 2/2015 |
| WO | 2013051568 A1 | 3/2015 |

OTHER PUBLICATIONS

Search Report dated Mar. 15, 2019 corresponding to European application No. 16841531.3.
International Preliminary Report on Patentability dated Mar. 6, 2018 corresponding to application No. PCT/JP2016/074221.
Office Action dated Feb. 23, 2019 corresponding to Taiwanese application No. 105127381.
Office Action dated Nov. 17, 2017 in U.S. Appl. No. 15/032,709.
Office Action dated Jul. 14, 2017 issued in corresponding Taiwanese Application No. 102145132.
European Search Report dated Nov. 21, 2016 corresponding to application No. 13864780.5-1501.
Search Report dated Nov. 22, 2016 in corresponding WO Patent Application No. PCT/JP2016/074221.
Notice of Allowance dated May 16, 2017 in corresponding with counterpart Japanese patent application No. P2014-553046.
International Patent application No. PCT/JP2013/081944, International Search Report dated Mar. 4, 2014, two (2) pages.
International Patent application No. PCT/JP2013/081944, International Preliminary Report on Patentability dated Jul. 2, 2015, seven (7) pages.
Office Action dated Jan. 24, 2017 for CN Counterpart application 201380071668.9.
European Search Report dated Sep. 27, 2017 in corresponding with not Counterpart European Patent Application No. 14859702.4.
Chinese Office Action dated Mar. 4, 2020 corresponding to application No. 201680050543.1.

* cited by examiner

APPLICATOR

This is a National Phase Application filed under 35 U.S.C. 371 as a national stage of PCT/JP2016/074221, filed Aug. 19, 2016, an application claiming the benefit of Japanese Application No. 2015-172793, filed Sep. 2, 2015, the content of each of which is hereby incorporated by reference in its entirety.

TECHNICAL FIELD

An aspect of the present invention relates to an applicator for applying microneedles to skin.

BACKGROUND ART

Applicators for applying microneedles for administrating active components through skin by giving impact to the microneedles have conventionally been known. For example, Patent Literature 1 below discloses an applicator that includes a flexible sheet having a raised central area attached to a microneedle device, and a supporting member provided at or near the periphery of the flexible sheet. The flexible sheet is configured to undergo a stepwise motion in a direction orthogonal to a major plane of the sheet.

With the applicator disclosed in Patent Literature 1 below, the central area of a flexible sheet acting on the microneedles is pushed directly by a user. Therefore, the force transmitted to the microneedles varies depending on the force the user applies. Therefore, the degree by which the microneedles are inserted is dependent on the force applied by users, and there might be cases in which the microneedles are not applied properly to the skin, or the reproducibility of insertion of the microneedles to the skin deteriorates. A possible countermeasure for such a problem includes the use of an applicator an example of which is disclosed in Patent Literature 2. This applicator includes an elastic member such as a spring for applying biasing force to the microneedle device, engagement means for keeping the elastic member having been compressed in the engaged condition, and release means the engagement of the elastic member.

CITATION LIST

Patent Literature

[Patent Literature 1] JP 2008-520369 A
[Patent Literature 2] JP 2005-533625 A

SUMMARY OF INVENTION

Technical Problem

When such an applicator is to be used, a user releases the engagement of the elastic member using the release means, so that predetermined biasing force generated by the elastic member is applied to the microneedle device. In this manner, theoretically, it is possible to eject the microneedle device out of the applicator at a stable speed, in a manner not depending on the force applied by a user. However, even with such an applicator, there might be a case in which the speed of the ejected microneedle device drops and the microneedle device is not applied properly to the skin.

Therefore, an object of one aspect of the present invention is to provide an applicator enabling microneedles to be applied appropriately to skin.

Solution to Problem

An applicator according to one aspect of the present invention is an applicator for applying microneedles to skin, and includes a housing having a tubular shape with one closed end, and configured to house an elastic member and a piston plate for transmitting biasing force of the elastic member to the microneedles, and release means configured to release the piston plate engaged in a manner resisting against the biasing force of the elastic member in the housing, to cause the piston plate to move toward an opening of the housing along an axial direction of the housing. The release means is configured, when the release means releases the engagement of the piston plate by moving toward the housing in the axial direction, to transmit force in a direction toward the opening to the housing.

With this applicator, when the release means releases the engagement of the piston plate, the piston plate receives the biasing force released as the elastic member restores the original shape. This biasing force moves the piston plate toward the opening of the housing in the axial direction. At the same time, the reactive force of the biasing force acts on the housing, as force to lift the housing. In the applicator described above, when the release means releases the engagement of the piston plate by moving toward the housing in the axial direction, the release means transmits the force in the direction toward the opening. Therefore, the reactive force acting on the housing is reduced advantageously, by the force transmitted to the housing by the release means when the engagement of the piston plate is released. Hence, the position of the housing can be stabilized while the piston plate is being moved by the biasing force, and a reduction in the moving speed of the piston plate can be suppressed, so that the microneedles can be applied properly to the skin.

Advantageous Effects of Invention

According to one aspect of the present invention, it is possible to provide an applicator enabling microneedles to be applied appropriately to skin.

BRIEF DESCRIPTION OF DRAWINGS

FIG. 5(*a*) is a plan view of a piston plate. FIG. 5(*b*) is a cross-sectional view across the line Vb-Vb in FIG. 5(*a*).

DESCRIPTION OF EMBODIMENTS

An embodiment of the present invention will be explained in detail below with reference to accompanying drawings. In the description of the drawings, the same or equivalent elements are denoted with the same reference signs, and a redundant description thereof will be omitted.

An applicator according to the embodiment is a device for administrating any active component such as a drug into a living body. Specifically, the applicator is a device that administrates active components to internal of skin, by applying the microneedles described later to the skin. Applying the microneedles to the skin means bringing the microneedles into contact with or inserting the microneedles into the skin.

Figure 1:
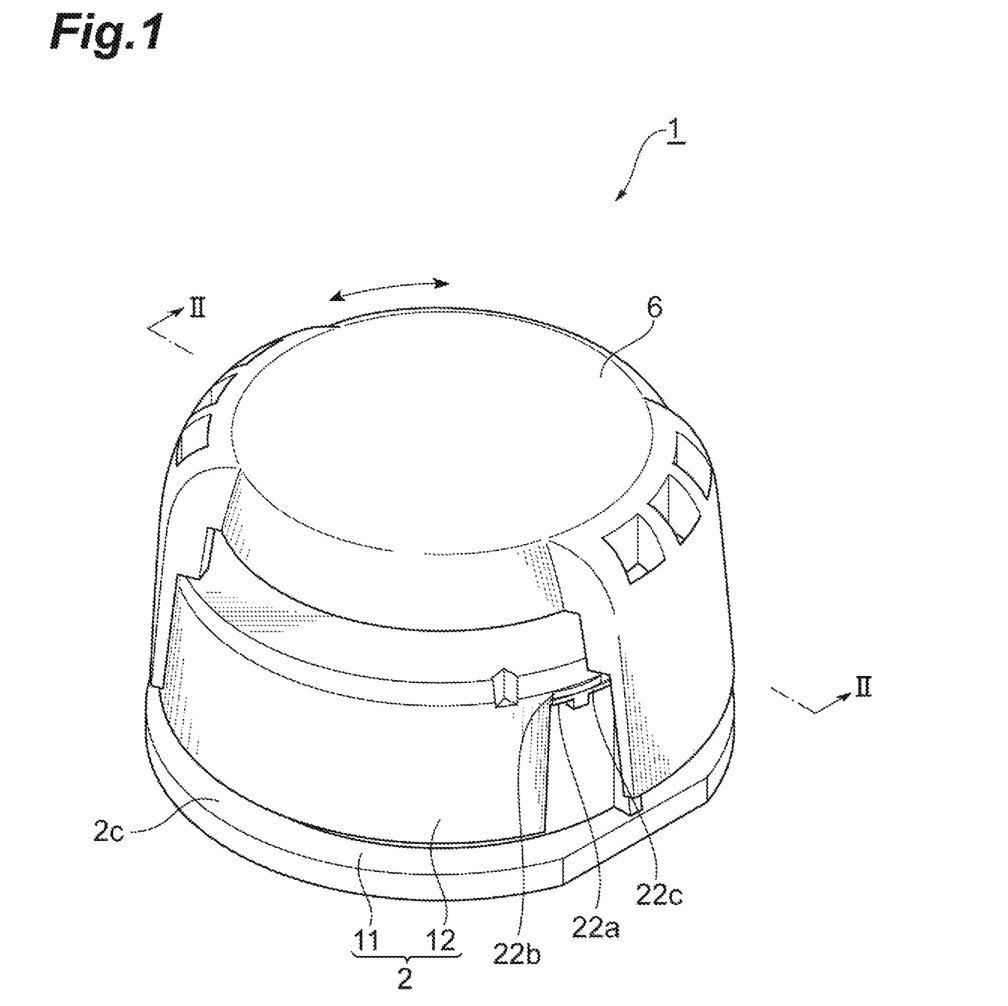
FIG. 1 is a perspective view illustrating an applicator according to an embodiment.
Figure 2:
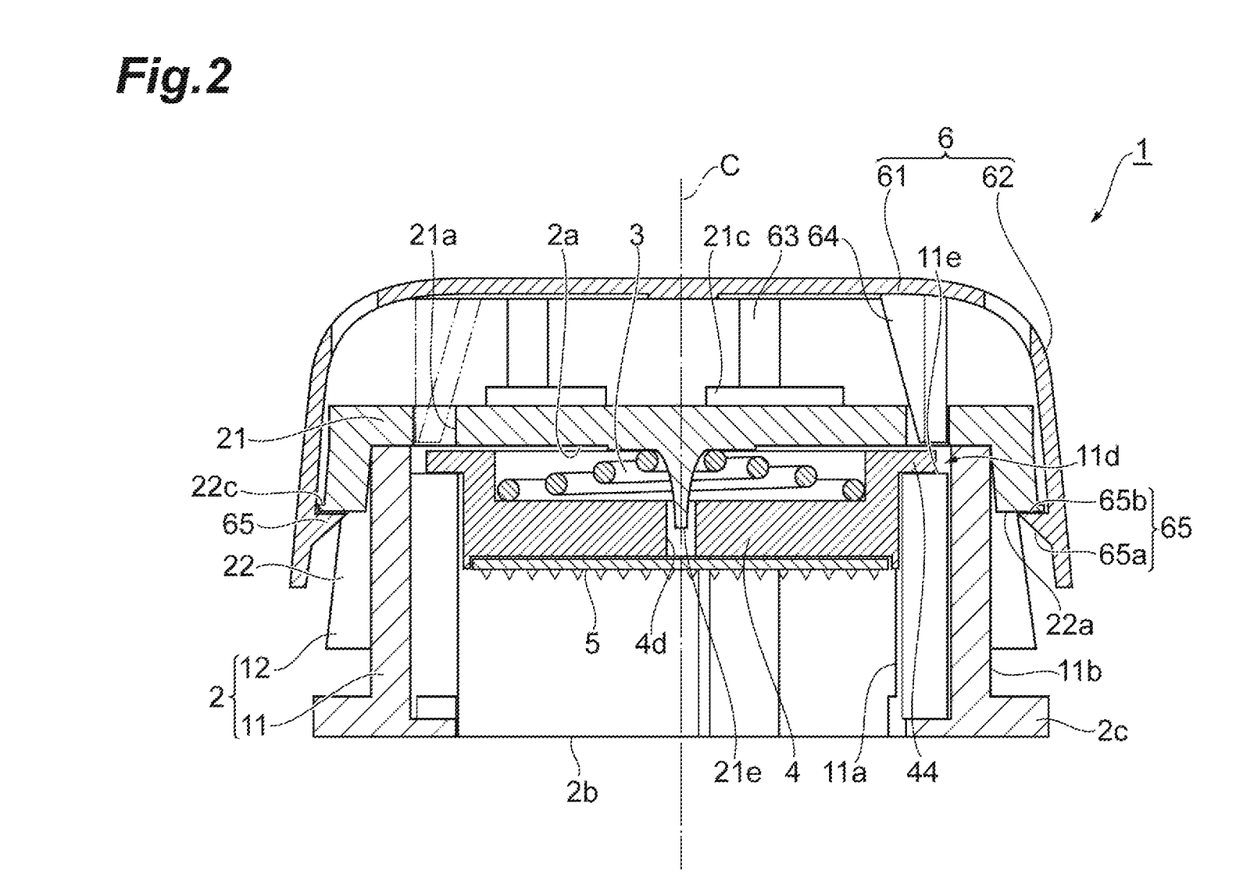
FIG. 2 is a cross-sectional view across the line II-II in FIG. 1.
Figure 3:
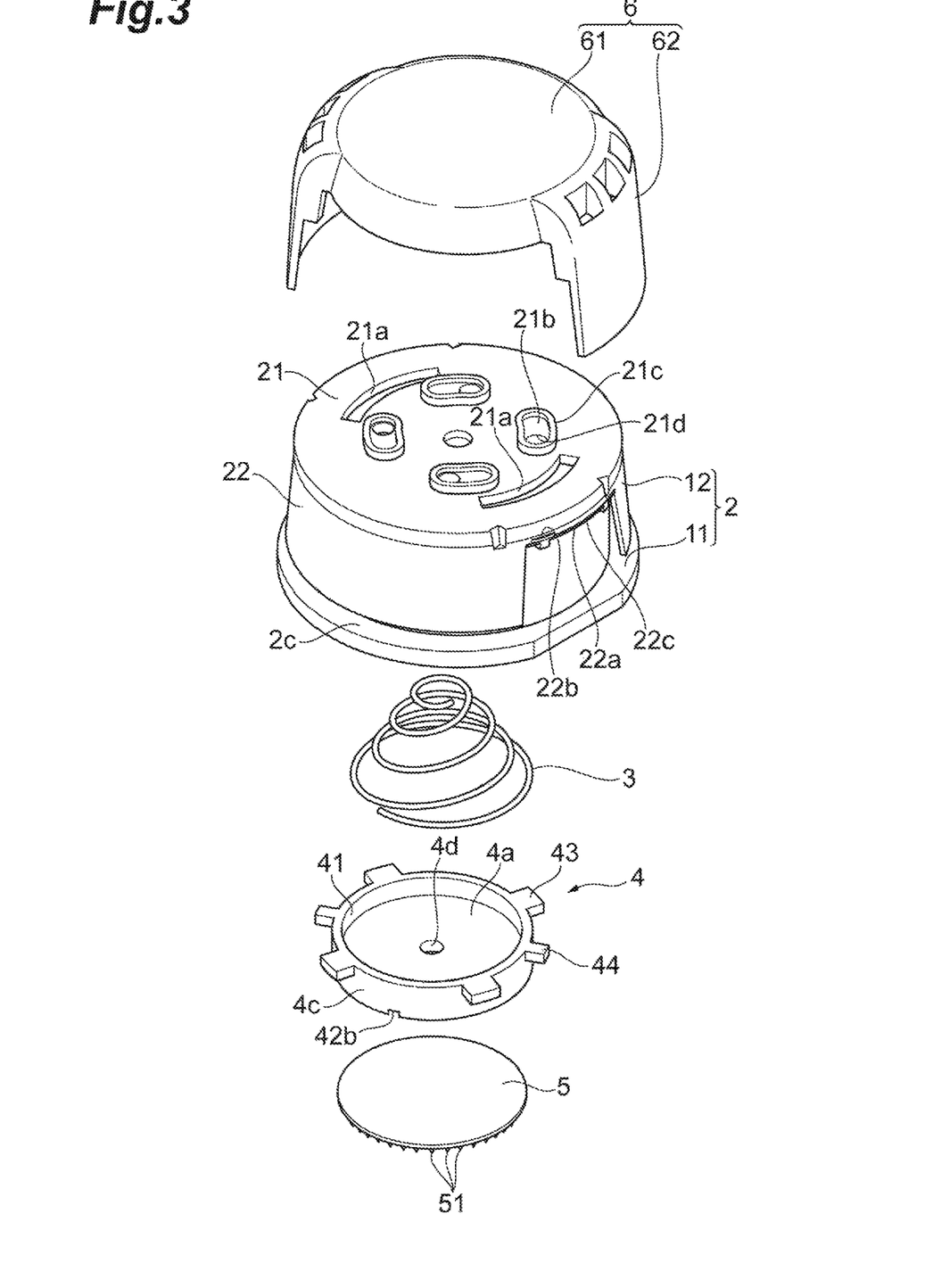
FIG. 3 is an exploded view of the applicator according to the embodiment.
Figure 4:
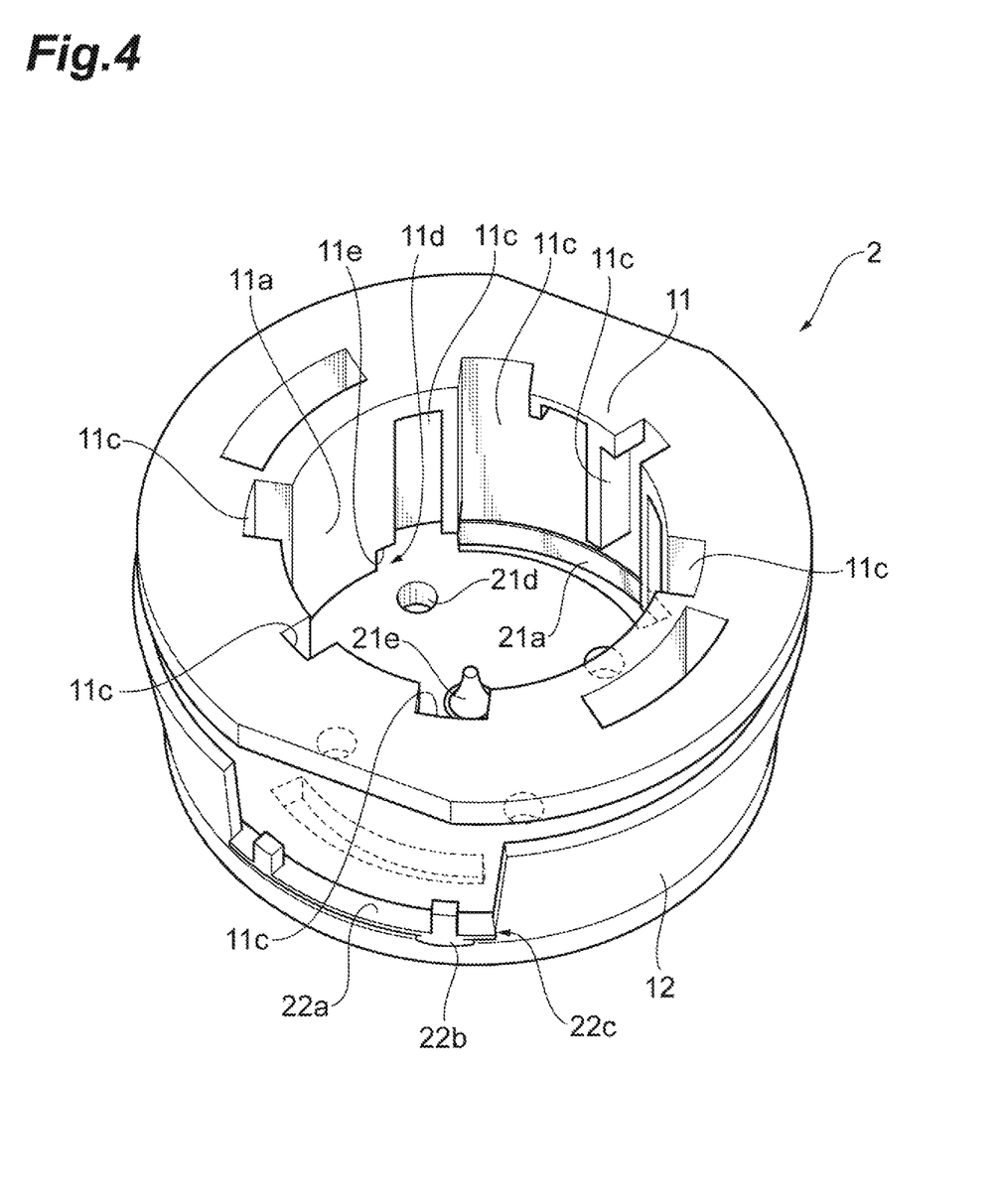
FIG. 4 is a perspective view of a housing of the applicator viewed from a bottom side.

FIG. 1 is a perspective view illustrating applicator according to the embodiment. FIG. 2 is a cross-sectional view across the line II-II in FIG. 1. FIG. 3 is an exploded view of the applicator according to the embodiment. FIG. 4 is a perspective view of the bottom surface of a housing of the applicator. As illustrated in FIGS. 1 to 4, the applicator 1 includes a housing 2 that has a hollow, a non-linear coil spring (elastic member) 3 and a piston plate 4 that are housed in the housing 2, a microneedle device 5 that is attached to the piston plate 4, and an actuation button (release means) 6 that is removably attached to the housing 2.

The materials of the housing 2, the piston plate 4, and the actuation button 6 included in the applicator 1 are not limited to any particular materials. For example, the housing 2, the piston plate 4, and the actuation button 6 may be fabricated from any synthetic resin material or natural resin material such as acrylonitrile butadiene styrene (ABS) resin, polystyrene, polypropylene, polyacetal (POM), polycarbonate, and polybutylene terephthalate (PBT). Alternatively, the housing 2, the piston plate 4, and the actuation button 6 may be fabricated from silicon, silicon dioxide, ceramic, or a metal (such as stainless steel, titanium, nickel, molybdenum, chromium, and cobalt). The materials from which the housing 2, the piston plate 4, and the actuation button 6 are fabricated may be the same or different from one another.

As illustrated in FIGS. 1 to 4, the housing 2 is a member with a tubular shape having one end closed and the other end with an opening. In the embodiment, the housing 2 includes a cylindrical body 11 and a lid 12 that covers one opening 2a of the body 11 and that is attached to the body 11. The other opening 2b of the housing 2 remains uncovered, and the inner circumferential surface 11a of the body 11 is exposed via the opening 2b. In the embodiment, the lid 12 is attached to the body 11 by fusion-bonding the lid 12 to the outer circumferential surface 11b of the body 11. An enlarged diameter portion 2c for allowing the housing 2 to be stably placed on the skin is provided to the periphery of the opening 2b of the body 11.

In the explanation hereunder, in the applicator 1, the side on which the opening 2a is positioned is defined as a top side (top-surface side), and the side on which the opening 2b is positioned is defined as a bottom side (bottom-surface side). An axis, illustrated in FIG. 2, passing through the center of the housing 2 and extending from the bottom side toward the top side is defined as the central axis C of the housing 2. This central axis C extends in a manner intersecting perpendicularly with the piston plate 4 that is housed in the housing 2. In the explanation hereunder, the direction in which the central axis C extends is defined as an axial direction, and the direction following the circumference of the central axis C is defined as a circumferential direction. Furthermore, in the explanation hereunder, the length of any member included in the applicator 1 in the axial direction is defined as a height, and the length in the circumferential direction is defined as a width.

As illustrated in FIG. 4, on the inner circumferential surface 11a of the body 11, a plurality of grooves 11c extending from the opening 2a toward the bottom side are provided. The widths of the grooves 11c may be the same or different from one another. The number of grooves 11c provided to the body 11 is determined by the numbers of first protrusions 43 and second protrusions 44 that are provided on the outer circumferential surface 4c of the piston plate 4 (the piston plate 4 will be described later in detail).

As illustrated in FIGS. 2 and 4, a clearance 11d transmitted with a groove 11c on the side of the opening 2a is provided in plurality. The surface defining the clearance 11d and extending orthogonally to the axial direction in the body 11 is defined as a stepped surface 11e that forms a step inside the body 11. The height of the clearance 11d (that is, the distance between the stepped surface 11e and the lid 12 in the axial direction) is substantially matched with the height of the largest one of the first protrusion 43 and the second protrusion 44 of the piston plate 4. By adjusting the height of the clearance 11d, the compression ratio of a coil spring 3, which is described later, in the axial direction can be adjusted.

As illustrated in FIGS. 2 and 3, the lid 12 includes a top plate 21 that covers the opening 2a on the top side, and a tubular portion 22 extending from the circumferential rim of the top plate 21 toward the bottom side. The top plate 21 has a plate-like shape with a size covering the opening 2a of the body 11 when being viewed along the axial direction. The top plate 21 has a substantially circular shape when being viewed along the axial direction, but the shape may also be a rectangular or polygonal shape. A pair of arc-shaped holes 21a are provided to the top plate 21. The pair of holes 21a is provided to the top plate 21 line-symmetrically to each other with respect to the central axis C, for example. A bank 21c surrounding each of the arc-shaped areas 21b is provided to the top surface of the top plate 21. Because the area 21b is provided in plurality along the circumferential direction when being viewed along the axial direction, the bank 21c, too, is provided in plurality. The areas 21b are arranged with a predetermined distance therebetween. A part of each of the areas 21b has a hole 21d. The number of the areas 21b, the banks 21c, and the holes 21d provided to the top plate 21 are not limited to any particular number, and the number may be one.

As illustrated in FIGS. 2 and 4, a central shaft (protruding portion) 21e protruding along the axial direction is provided to the bottom surface of the top plate 21. This central shaft 21e is provided along the central axis C. The height of the central shaft 21e may be set to any length as long as that the central shaft 21e does not completely penetrate through a hole 4d provided to the piston plate 4 described later, and is not brought into contact with the microneedle device 5.

As illustrated in FIGS. 1 to 3, a pair of recessed portions 22a are provided to portions of the tubular portion 22 of the lid 12. The recessed portions 22a are recessed in a manner extending from the bottom side toward the top side of the tubular portion 22. The depth of the recessed portions 22a (the length along the axial direction) is not limited to any particular size, as long as there is some remaining part of the tubular portion 22 between the top plate 21 and the recessed portion 22a. The pair of recessed portions 22a are provided line-symmetrically to each other with respect to the central axis C, for example.

As illustrated in FIGS. 1, 3, and 4, in the tubular portion 22, a bulged portion 22b is provided to a part of the area between the recessed portion 22a and the top plate 21 (that is, the outer circumference of the housing 2). This bulged portion 22b is a portion bulging in a direction moving away from the central axis C. The top end surface of the bulged portion 22b extends in a manner intersecting with the axial direction. More precisely, the top end surface of the bulged portion 22b may extend in a manner intersecting perpendicularly with the axial direction. The bulged portion 22b is enabled to be brought into contact with a second engaging portion 66 of the actuation button 6, which will be described later (see FIG. 6). The amount by which the bulged portion 22b bulges may be changed in a continuous manner along the circumferential direction.

As illustrated in FIGS. 1, 3, and 4, in the tubular portion 22, an eave portion 22c is provided in a manner extending along the upper end of the recessed portion 22a, the upper end being positioned on the side of the top plate 21. The eave portion 22c can be brought into contact with the top surface 65b of a first engaging portion 65 of the actuation button 6 (see FIG. 6), which will be described later, and can be brought into contact with the second engaging portion 66 of the actuation button 6 (see FIG. 6). The eave portion 22c may be provided in a manner integrated with the bulged portion 22b.

As illustrated in FIGS. 2 and 3, the coil spring 3 is a non-linear spring wound in a truncated cone shape, and is housed in the housing 2 in a manner held in contact with the bottom surface of the top plate 21. The coil spring 3 is arranged in a manner surrounding the central shaft 21e, and is compressed by the lid 12 and the piston plate 4 in the housing 2. In this manner, the coil spring 3 is arranged inside the housing 2, with the biasing force thereof stored, and with the position thereof adjusted by the central shaft 21e. The material of which the coil spring 3 is made is not limited to a particular material, but the coil spring 3 is made from, for example, a stainless-steel wire, an iron wire, or a copper wire.

Figure 5:
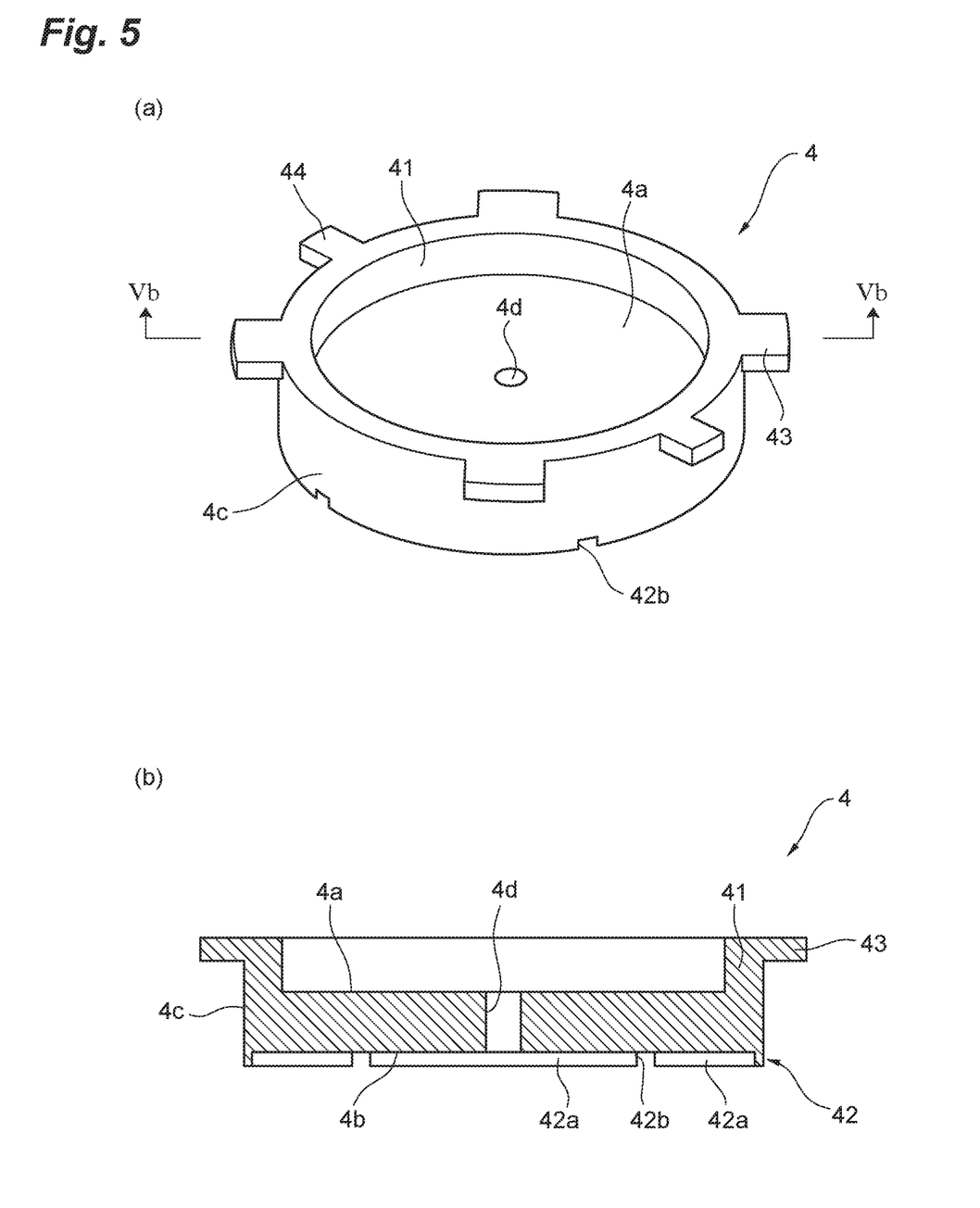

The (a) of FIG. 5 is a plan view of the piston plate. The (b) of FIG. 5 is a cross-sectional view across the line Vb-Vb in (a) of FIG. 5. As illustrated in FIGS. 2 to 5, the piston plate 4 is a plate-like member for transmitting the biasing force of the coil spring 3 to the microneedle device 5. The piston plate 4 has a planar shape corresponding to the shape of the inner circumferential surface 11a of the body 11 viewed from the bottom side. In other words, the piston plate 4 has substantially circular principal surfaces 4a, 4b, when being viewed along the axial direction. The outer circumferential surface 4c of the piston plate 4 may be or may not be brought into contact with the inner circumferential surface 11a of the body 11. A hole 4d that is a through hole is provided to the center of the piston plate 4. As illustrated in FIG. 2, the central shaft 21e fits inside hole 4d.

The upper principal surface 4a of the piston plate 4 is a surface that faces the lid 12 of the housing 2. A bank 41 is provided on the principal surface 4a, along the circumferential rim of the principal surface 4a. The height of the bank 41 is set to any height less than the uncompressed coil spring 3. When the heights of the clearances 11d provided to the body 11 are constant, the compression ratio of the coil spring 3 in the axial direction can be adjusted by adjusting the height of the bank 41.

On the bottom principal surface 4b of the piston plate 4, a bank 42 having a plurality of protruding portions 42a is provided. Each of the protruding portions 42a has substantially an arc shape when being viewed along the axial direction, and is provided along the circumferential rim of the principal surface 4b. Each of the protruding portions 42a has a substantially rectangular cross section. The protruding portions 42a are separated from one another, and clearances 42b are provided therebetween. These clearances 42b are provided, for example, to align a jig for inserting the piston plate 4 into the housing 2.

On the top side of the outer circumferential surface 4c of the piston plate 4, a plurality of first protrusions 43 and a pair of second protrusions 44, both protruding outwards from the outer circumferential surface 4c, are provided. For example, the first protrusions 43 and the second protrusions 44 are provided to the outer circumferential surface of the bank 41 of the piston plate 4. The first protrusions 43 are provided at a constant interval, along the circumferential direction of the piston plate 4. The second protrusions 44 are provided line-symmetrically to each other with respect to the central axis C. The heights of the first protrusions 43 and the second protrusion 44 may be the same or different with respect to one another. The height of the first protrusions 43 and the second protrusion 44 may correspond to the height of the bank 41, or less than the height of the bank 41. The width of the first protrusions 43 is different from the width of the second protrusions 44. The width of the first protrusions 43 is larger than the width of the second protrusions 44. In the housing 2, the first protrusions 43 are disposed inside the respective clearances 11d, and, when the piston plate 4 is to be attached to the housing 2, the first protrusions 43 are placed on the respective stepped surfaces 11e. Therefore, these first protrusions 43 and stepped surfaces 11e of the body 11 obstruct the movement of the piston plate 4 toward the bottom side, the movement being caused by the biasing force of the coil spring 3. In other words, the piston plate 4 is thus engaged in the housing 2 in a manner resisting against the biasing force of the coil spring 3. The piston plate 4 is engaged by inserting the piston plate 4 into the housing 2, rotating the piston plate 4 in the circumferential direction, and placing the first protrusions 43 on the stepped surfaces 11e.

The microneedle device 5 is fixed to the principal surface 4b of the piston plate 4. The method by which the microneedle device 5 is fixed to the piston plate 4 is not limited to a particular method, and the microneedle device 5 may be fixed to the piston plate 4 using adhesive agent, for example. The microneedle device 5 may be fixed to the piston plate 4 from the beginning, or may be fixed to the piston plate 4 by a user. It is not mandatory for the applicator 1 to be provided with the microneedle device 5. As illustrated in FIGS. 2 and 3, the microneedle device 5 is a plate-like member having a bottom principal surface provided with a plurality of microneedles 51. The material of the microneedle device 5 is not limited to any material, and the microneedle device 5 is fabricated from any one of stainless steel, polyethylene terephthalate (PET), any other metals, any other resins, biodegradable materials, ceramic, or bioabsorbable materials, or any combination thereof; for example. The length of these microneedles 51 is 10 μm to 1000 μm, for example. The density of the microneedles 51 is $0.05/cm^2$ to $10000/cm^2$, for example. The microneedles 51 extend in the axial direction.

In the embodiment, it does not matter whether or not the microneedles 51 are coated with an active component in advance. When the microneedles 51 are not coated with the active component, the active component may be administrated by applying the active component onto the skin, and then applying the microneedle device 5 onto the area using the applicator 1. It is also possible to administrate the active component by applying the microneedle device 5 to the skin using the applicator 1, and then applying the active component to the area applied with the microneedle device 5.

As illustrated in FIGS. 1 to 3, the actuation button 6 is attached to the housing 2 on the top side of the lid 12, in a rotatable manner in the circumferential direction. The actuation button 6 is a member for releasing the piston plate 4 that is engaged in the housing 2 in a manner resisting against the biasing force of the coil spring 3, to cause the piston plate 4 to move toward the other opening 2b along the axial direction of the housing 2. The actuation button 6 includes a plate-like pressing portion 61 that is pressed when a user uses the applicator 1, and a pair of attaching portions 62 extending from the rim of the pressing portion 61 toward the bottom side. The pressing portion 61 and the attaching portions 62 are formed integrally. The pressing portion 61 is a plate-like member having a size for covering the opening 2a of the body 11 when being viewed along the axial direction. The pressing portion 61 has a circular shape when being viewed along the axial direction, but may also have a rectangular or polygonal shape. The pair of attaching portions 62 are positioned in a line-symmetry to each other with respect to the central axis C.

Figure 6:
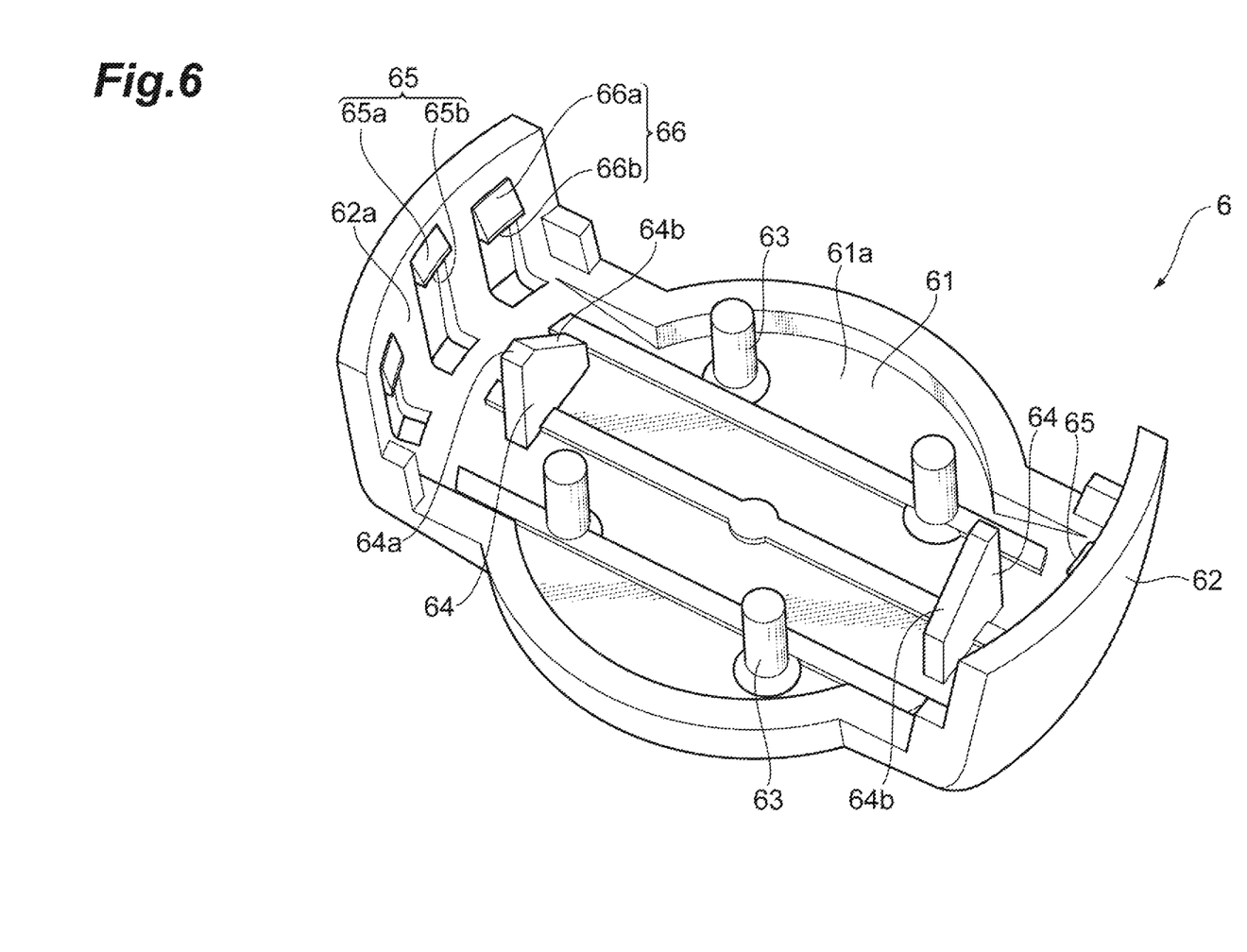
FIG. 6 is a schematic of an actuation button viewed from the bottom side.

FIG. 6 is a schematic of the actuation button 6 viewed from the bottom side. As illustrated in FIG. 6, a plurality of protruding portions 63 are provided, and a pair of piston plate pushing portions (release portion) 64 are provided to a rear surface 61a of the pressing portion 61. The protruding portions 63 are substantially columnar-shaped portions protruding from the rear surface 61a toward the bottom side. Each of the protruding portions 63 are provided in a manner positioned above the corresponding area 21b. Therefore, the number of protruding portions 63 corresponds to the number of the banks 21c. The diameter of the protruding portion 63 is set in such a manner that the protruding portion 63 fits inside the bank 21c and passes through the hole 21d. The tip of the protruding portion 63 may be or may not be brought into contact with the area 21b.

The piston plate pushing portions 64 are plate-like portions that protrude from the rear surface 61a, and have a substantially triangle shape tapered toward the bottom side. The piston plate pushing portion 64 has a top surface 64a extending in parallel with the rear surface 61a, and an inclined surface 64b extending in an inclined manner from the rear surface 61a toward the top surface 64a. Because the inclined surface 64b is a surface extending in a direction intersecting with the circumferential direction, the width of the piston plate pushing portion 64 in the circumferential direction becomes smaller toward the tip. As illustrated in FIG. 2, the piston plate pushing portions 64 are inserted into the respective holes 21a provided to the top plate 21. Therefore, the number of the piston plate pushing portions 64 corresponds to the number of the holes 21a. The height of the piston plate pushing portions 64 is greater than the height of the protruding portions 63. The inclined surface 64b of the piston plate pushing portion 64 is enabled to be brought into contact with the second protrusion 44.

As illustrated in FIG. 6, the first engaging portion 65 and the second engaging portions (engaging portions) 66 are provided to a rear surface 62a of the attaching portion 62. The first engaging portion 65 is a hook-shaped portion protruding from the rear surface 62a toward the central axis C. The first engaging portion 65 has an inclined surface 65a inclined in a manner approaching the central axis C from the bottom end toward the top end thereof, and a top surface 65b extending from the top end of the inclined surface 65a toward the rear surface 62a. The top surface 65b extends in parallel with the rear surface 61a, but may also extend in a manner intersecting with the rear surface 61a. The first engaging portion 65 is provided near the bottom end of the attaching portion 62. As illustrated in FIG. 2, as the first engaging portion 65 enters the recessed portion 22a, and the top surface 65b of the first engaging portion 65 hooks onto the recessed portion 22a, the first engaging portion 65 becomes engaged with the recessed portion 22a. The width of the first engaging portion 65 is set smaller than the width of the recessed portion 22a.

The second engaging portion 66 is a hook-shaped portion protruding from the rear surface 62a toward the central axis C, in the same manner as the first engaging portion 65. The second engaging portion 66 has an inclined surface 66a inclined in a manner approaching the central axis C from the bottom end toward the top end thereof, and a top surface 66b extending from the top end of the inclined surface 66a toward the rear surface 62a. The top surface 66b extends in parallel with the rear surface 61a, but may also extend in a manner intersecting with the rear surface 61a. The second engaging portion 66 is provided between the first engaging portion 65 and the pressing portion 61 in the axial direction. In other words, the second engaging portion 66 is positioned on the top side of the first engaging portion 65. The second engaging portion 66 may be brought into contact with the outer circumferential surface of the lid 12, with the actuation button 6 attached to the housing 2. Two second engaging portions 66 are provided to each of the attaching portions 62, but one, or three or more second engaging portions 66 may also be provided.

An action of the applicator 1 according to the embodiment will now be explained. Particularly, an operation of releasing the engagement of the piston plate 4 when a user uses the applicator 1, and the change in the engagement of the actuation button 6 with respect to the applicator 1 will be explained. In the explanation hereunder, it is assumed that the applicator 1 is installed in advance in such a manner that the bottom surface of the applicator 1 is in contact with skin of a living body. It is also assumed that the user is to use the applicator 1 having been set to a locked condition, as an initial condition. The locked condition is a condition where the release of the piston plate 4 by the actuation button 6 is prohibited. Specifically, the locked condition is a condition where the protruding portions 63 of the pressing portion 61 are positioned inside the respective areas 21b of the top plate 21 in the axial direction. Even if the pressing portion 61 is pressed toward the bottom side in the locked condition, the protruding portions 63 are brought into contact with the top plate 21, so that the movement of the actuation button 6 toward the bottom side is obstructed.

As described earlier, the actuation button 6 is attached to the housing 2. More specifically, each of the first engaging portions 65 is engaged with the corresponding recessed portion 22a and bottom end of the eave portion 22c of the lid 12. Because the width of the first engaging portions 65 is smaller than the recessed portions 22a, the actuation button 6 is allowed to rotate in the circumferential direction within a certain range. The rotatable range of the actuation button 6 is defined by the circumferential length of the areas 21b of the top plate 21, across which the protruding portions 63 of the pressing portion 61 move.

To begin with, a user unlocks the locked condition by rotating the actuation button 6 attached to the housing 2 in the circumferential direction (unlocked condition). The unlocked condition is a condition where the engagement of the piston plate 4 can be released by the actuation button 6. Specifically, the unlocked condition is a condition where the protruding portions 63 are brought to the positions above the respective holes 21d on the top plate 21, by rotating the actuation button 6. In the unlocked condition, when the pressing portion 61 is pressed toward the bottom side, the protruding portions 63 are not brought into contact with the top plate 21, and therefore, the actuation button 6 can be moved toward the bottom side at any time. Furthermore, in the unlocked condition, the inclined surface 66a of each of the second engaging portions 66 is brought into contact with the top end of the corresponding eave portion 22c of the lid 12. Therefore, the second engaging portions 66 are supported by the respective eave portions 22c, and the actuation button 6 in the unlocked condition does not automatically move toward the bottom side. When the actuation button 6 is rotated in the circumferential direction, the second engaging portions 66 are forced over the respective bulged portions 22b, and reach the unlocked condition. The actuation button 6 can be maintained in the unlocked condition by these bulged portions 22b, and the bulged portions 22b prevent the actuation button 6 from going back to the locked condition unexpectedly. In the embodiment, the four second engaging portions 66 are provided in total on the actuation button 6, and the two bulged portions 22b and the two eave portions 22c are provided in total on the housing 2. In the locked condition, a part of the second engaging portion 66 is supported by the corresponding eave portion 22c.

The user then presses the pressing portion 61 of the actuation button 6 toward the bottom side, and causes the actuation button 6 to move toward the bottom side. At this time, because the protruding portions 63 of the pressing portion 61 are inserted into the respective holes 21d, the movement of the actuation button 6 is not obstructed. As the actuation button 6 moves, the piston plate pushing portions 64, which are configured to pass through the respective holes 21a, enter the respective holes 21a of the body 11. When the piston plate pushing portions 64 enter the respective holes 21a, the inclined surfaces 64b of the piston plate pushing portions 64 are brought into contact with the second protrusions 44 of the piston plate 4.

Figure 7:
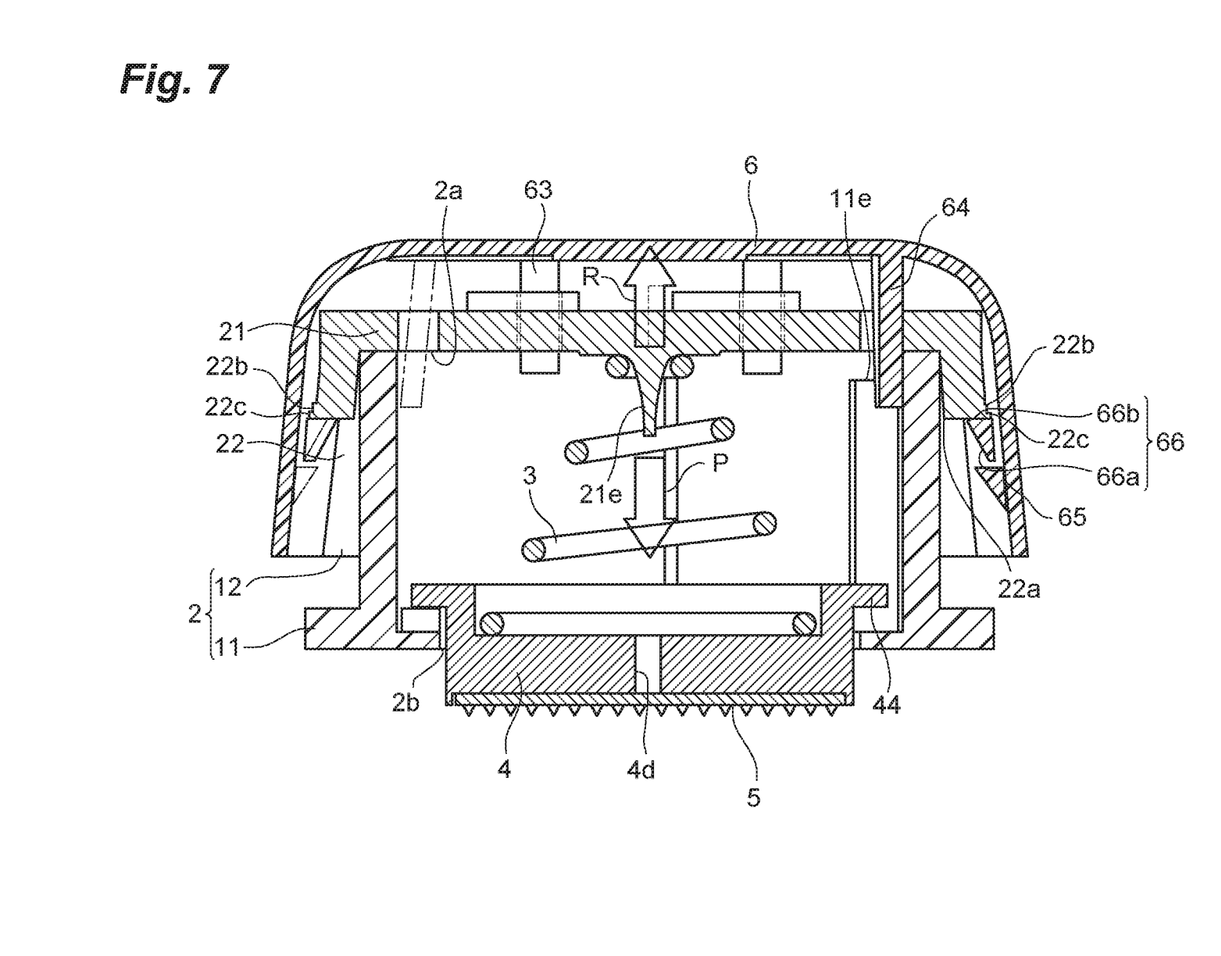
FIG. 7 is a cross-sectional view illustrating the applicator after the engagement of the piston plate has been released.

As described earlier, the piston plate pushing portions 64 have a width gradually becoming smaller toward the tip. Therefore, as the piston plate pushing portion 64 is carried further inside the hole 21a, the width of the piston plate pushing portion 64 at the level where piston plate pushing portion 64 is brought into contact with the second protrusion 44 increases, and the second protrusions 44 is pushed away in the circumferential direction. As the second protrusions 44 moves in the circumferential direction, the piston plate 4 is caused to rotate about the central axis C in the circumferential direction, and the first protrusions 43 are caused to move out of the clearances 11d and to enter the respective grooves 11c. At this time, the second protrusions 44 are positioned in the corresponding grooves 11c. In this manner, the contacts between the first protrusions 43 and the respective stepped surfaces 11e of the body 11 are removed, and the stepped surfaces 11e of the body 11 no longer prevent the biasing force of the coil spring 3 from moving the piston plate 4 toward the bottom side. Therefore, as the actuation button 6 moves toward the bottom side, the engagement achieved by the first protrusions 43 and the second protrusions 44 of the piston plate 4 is released, and the piston plate 4 receiving the biasing force P of the coil spring 3 moves toward the bottom side, as illustrated in FIG. 7. At this time, the piston plate 4 moves toward the bottom side, by being guided by the first protrusions 43 having entered the corresponding grooves 11c and the central shaft 21e inside the hole 4d. As the piston plate 4 moves, the microneedle device 5 pierces the skin of the living body. Furthermore, reactive force R of the biasing force P generated by the coil spring 3 acts on the lid 12.

As the actuation button 6 for releasing the engagement of the piston plate 4 moves, the second engaging portions 66 are also moved in the axial direction, forced over the top ends of the respective eave portions 22c, and become engaged with the respective recessed portions 22a and bottom ends of the eave portions 22c. In this manner, even after the engagement of the piston plate 4 is released, the actuation button 6 is kept fixed to the housing 2. Therefore, when a user releases the engagement of the piston plate 4, the force applied to the actuation button 6 by the user is transmitted properly from the actuation button 6 to the housing 2, and the reactive force R is transmitted properly from the housing 2 to the actuation button 6. As a result, the force that is applied by the user to the actuation button 6 and that is transmitted to the housing 2 is cancelled by the reactive force R in the housing 2. Therefore, lifting of the housing 2 can be suppressed.

In the embodiment, the second engaging portions 66 become engaged with the respective recessed portions 22a and bottom ends of the eave portions 22c at the same time as when the engagement of the piston plate 4 is released. However, the second engaging portions 66 may become engaged with the respective recessed portions 22a and bottom ends of the eave portions 22c after the engagement of the piston plate 4 is released. When the second engaging portions 66 are configured to become engaged with the respective recessed portions 22a and bottom ends of the eave portions 22c after the engagement of the piston plate 4 is released, the second engaging portions 66 may become engaged with recessed portions 22a and bottom ends of the eave portions 22c while the piston plate 4 is moving.

As explained above, the applicator according to one aspect of the present invention is an applicator for applying microneedles to skin, and includes a housing having a tubular shape with one closed end, and configured to house an elastic member (e.g., the coil spring 3 described in the embodiment); a piston plate configured to transmit the biasing force of the elastic member to microneedles; and release means (e.g., the actuation button 6 described in the embodiment) configured to release the piston plate engaged in a manner resisting against the biasing force of the elastic member in the housing, to cause the piston plate to move toward an opening of the housing along an axial direction of the housing. When the release means releases the engagement of the piston plate by moving toward the housing in the axial direction, the release means transmits the force in the direction toward the opening.

According to such an aspect, when the release means releases the engagement of the piston plate, the piston plate receives the biasing force released as the elastic member restores the original shape. This biasing force moves the piston plate toward the opening of the housing in the axial direction. At the same time, the reactive force of the biasing force acts on the housing, as force to lift the housing. In the applicator described above, when the release means releases the engagement of the piston plate by moving toward the housing in the axial direction, the release means transmits the force in the direction toward the opening. Therefore, the reactive force acting on the housing is reduced advantageously, by the force transmitted to the housing by the release means when the engagement of the piston plate is released. Hence, the position of the housing can be stabilized while the piston plate is being moved by the biasing force, and a reduction in the moving speed of the piston plate can be suppressed. Therefore, the microneedles can be applied properly to the skin.

Furthermore, the piston plate may also be provided with a hole, and the housing may be provided with a protruding portion fitting inside the hole and protruding in the axial direction. In such a configuration, the alignment of the piston plate in the engaged condition can be easily established. In addition, the piston plate can be rotated stably about the axial direction in the circumferential direction, with the position thereof restricted by the protruding portion. Furthermore, when the piston plate starts being moved, the piston plate can be moved stably along the protruding portion.

Furthermore, the release means may also include a release portion configured to release the engagement of the piston plate (e.g., the piston plate pushing portions 64 as described in the embodiment), and the engagement of the piston plate may be released by causing the release portion to rotate the piston plate, when the release means moves in the axial direction. In such a case, the engagement of the piston plate can be released without changing the axial position of the piston plate in the housing. Therefore, the engagement of the piston plate can be released without reducing the biasing force of the elastic member.

Furthermore, the release means may include an engaging portion, and the engaging portion may be configured to move in the axial direction and to become engaged with the housing, when the release means releases the engagement of the piston plate. In such a configuration, the release means becomes fixed to the housing via the engaging portion while the engagement of the piston plate is released. Therefore, the force applied to the release means at the time of releasing the engagement of the piston plate is transmitted properly to the housing, so that the reactive force acting on the housing is reduced more properly.

Furthermore, an eave portion may be provided to the outer circumferential surface of the housing, and the locked condition and the unlocked condition are switched when the release means rotates in the circumferential direction of the housing, and the locked condition is a condition where the release means is prohibited from releasing the engagement of the piston plate, and the unlocked condition is a condition at which the release means is permitted to release the engagement of the piston plate and the engaging portion may then be supported by the eave portion in the unlocked condition. In such a configuration, it is possible to reduce the chances of the engagement of the piston plate becoming automatically released in the unlocked condition.

The present invention is explained in detail above, based on one embodiment thereof. However, the present invention is not limited to the embodiment described above. Various modifications of the present invention are still possible within the scope not deviating from the essence of the present invention. The present invention is not limited to the embodiment described above.

For example, in the applicator 1 according to the embodiment described above, the speed at which the microneedle device 5 (the piston plate 4) moves is not limited to any particular speed, but the speed may be, for example, equal to or higher than 4 m/s or equal to or higher than 5 m/s, and equal to or lower than 30 m/s, equal to or lower than 15 m/s, or equal to or lower than 12 m/s. When the speed is equal to or lower than 12 m/s, the speed is lower than that of the microneedle device included in applicators that are generally used. In other words, the momentum (energy) applied to the microneedle device 5 according to the embodiment is smaller than that applied to a general microneedle device. In such a configuration, because the biasing force pushing out the microneedle device 5, and the reactive force of the biasing force become smaller, lifting of the housing 2 while the biasing force moves the piston plate 4 can be further suppressed. Therefore, the microneedles can be inserted more properly to the skin, and active components can be administrated more effectively while avoiding variation.

In the embodiment described above, the non-linear coil spring 3 is used as the elastic member, but the embodiment is not limited thereto. For example, various types of elastic member such as a linear coil spring or rubber may be used.

Furthermore, the applicator according to the embodiment described above may further include force transmission means that is provided between the housing 2 and the actuation button 6 (the release means). The force transmission means is held in a manner sandwiched between the top plate 21 of the housing 2 and the pressing portion 61 of the actuation button 6, for example. In such a configuration, when the release means releases the engagement of the piston plate, the release means presses the housing via the force transmission means. In this manner, the force applied to the release means is transmitted properly to the housing, without obstructing the movement of the release means in the axial direction. Therefore, the reactive force having acted on the housing can be reduced more appropriately. As the force transmission means, various types of elastic member such as a non-linear coil spring, a linear coil spring, or rubber may be used. When the applicator 1 includes the force transmission means, the second engaging portions 66 of the actuation button 6 may be omitted. Even in such a configuration, the microneedles can be applied properly to the skin, because the position of the housing 2 is stabilized while the biasing force moves the piston plate 4 and a reduction in the speed at which the piston plate 4 moves can be suppressed.

In the embodiment described above, the housing 2 is formed by fusion-boding the body 11 and the lid 12, but the embodiment is not limited thereto. For example, a structure corresponding to the combination of the body 11 and the lid 12 may be integrally formed. In such a configuration, a housing with one end closed can be formed, without forming an opening corresponding to the opening 2a.

In the embodiment described above, the first engaging portions 65 and the second engaging portions 66 have a hook-like shape, and are engaged with the recessed portions 22a, but the embodiment is not limited thereto. For example, the first engaging portions 65 and the second engaging portions 66 may be simple protrusions, not having a hook-like shape. Furthermore, the lid 12 may be provided with openings instead of the recessed portion 22a, and the first engaging portions 65 and the second engaging portions 66 may be engaged with the openings.

In the embodiment described above, the central shaft 21e is provided to the top plate 21 of the lid 12, but the configuration is not limited thereto. For example, a protruding portion extending toward the top plate 21 may be provided to the center of the principal surface 3a of the piston plate 4. In such a case, a hole capable of housing the protruding portion is provided to the center of the top plate 21. It is also possible to provide a protruding portion not overlapping with the central axis C to the rear surface of the top plate 21. In such a configuration, because the piston plate 4 is enabled to rotate in the circumferential direction, the hole provided to the piston plate 4 will have an arc shape when being viewed along the axial direction. The number of the protruding portions may be one or more. The protruding portion provided to the top plate 21 may be omitted, and in such a configuration, it is not necessary to provide the hole 4d to the piston plate 4.

In the embodiment described above, the bulged portions 22b are provided to the outer circumference of the housing 2, but the bulged portions 22b do not always need to be provided. Furthermore, the number of bulged portions 22b may be matched with the number of second engaging portions 66.

In the embodiment described above, the eave portions 22c are provided to the outer circumference of the housing 2, but the eave portions 22c do not always need to be provided.

In the embodiment described above, the piston plate 4 and the microneedle device 5 are provided as separate units, but the piston plate 4 may also be integrated with the microneedle device 5. In other words, the microneedles may be provided to the principal surface 4b of the piston plate 4.

In the embodiment described above, the actuation button 6 is used as a releasing member, but the embodiment is not limited thereto, and any other means may also be used. Furthermore, in the embodiment, the rotatable range of the actuation button 6 is defined by a relation between the protruding portion 63 and the area 21b surrounded by the bank 21c, but the embodiment is not limited thereto. For example, the rotatable range of the actuation button 6 may be defined by a relation between the piston plate pushing portion 64 provided to the pressing portion 61 and the hole 21a provided to the top plate 21.

Figure 8:
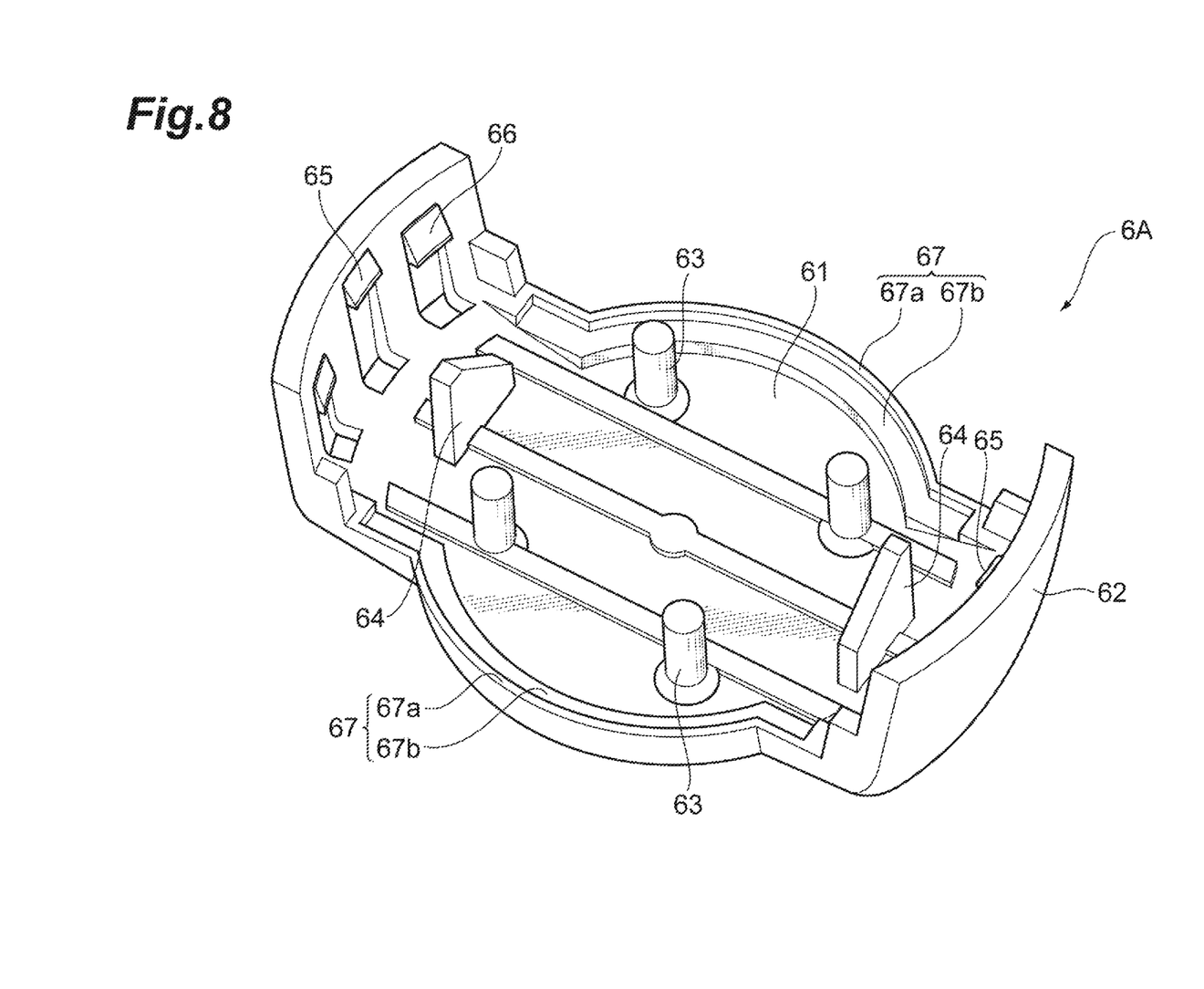
FIG. 8 is a schematic of an actuation button according to a modification viewed from the bottom side.

The actuation button 6 may also be modified to an actuation button 6A as illustrated in FIG. 8. The actuation button 6A is different from the actuation button 6 in that the arc-shape rim of pressing portion 61 has a stepped shape. The rim 67 of the actuation button 6A includes an outer rim 67a, and an inner rim 67b that is positioned on the inner side of the outer rim 67a and that has a height that is lower than that of the outer rim 67a. By providing the rim 67 with such a step-like shape, it is possible to reduce the area of the rim 67 that is brought into contact with the top plate 21 of the housing 2, when the actuation button 6A is pressed, so that the noise generated by the contact can be reduced. This configuration can contribute to the reduction of noise at the time of actuating the applicator. A specific shape of the step-shaped rim of the pressing portion 61 is not limited to the example illustrated in FIG. 8. For example, it is possible to form a step-shaped rim in which a high-level portion and a low-level portion are arranged alternatingly along the circumferential direction of the pressing portion 61 (that is, a rim having a comb-teeth shape).

As mentioned earlier, the top surface 66b of the second engaging portion 66 may extend in a manner intersecting with the rear surface 61a. By forming the top surface 66b in such a manner, it is possible to reduce the noise generated when the second engaging portions 66 become engaged with the recessed portions 22a and the bottom ends of the eave portions 22c, at the same time or after the engagement of the piston plate is released. This configuration can also contribute to the noise reduction at the time of actuating the applicator.

In order to reduce the noise at the time of actuating the applicator, at least one of the step-shaped rim 67 and the top surface 66b extending in a manner intersecting with the rear surface 61a may be used.

It is also possible to devise a prevention for the piston plate 4 in the locked condition from being rotated unexpectedly. Specifically, the width of the second protrusions 44 and the height of the piston plate pushing portions 64 are increased. The height of the piston plate pushing portions 64 are set in such a manner that the bottom end of the piston plate pushing portion 64 is positioned at a level lower than the top end of the second protrusions 44, when the applicator 1 is viewed in the horizontal direction. By setting the width of the second protrusions 44 and the height of the piston plate pushing portions 64 in the manner described above, the rotation of the piston plate 4 is obstructed by the second protrusions 44 being brought into contact with the piston plate pushing portions 64. Therefore, the piston plate 4 is not rotated even when vibrations (e.g., vibrations generated during the transportation of the applicator 1) is transmitted to the applicator 1 in the locked condition. This mechanism can reliably prevent the piston plate 4 from being released unexpectedly by itself.

Figure 9:
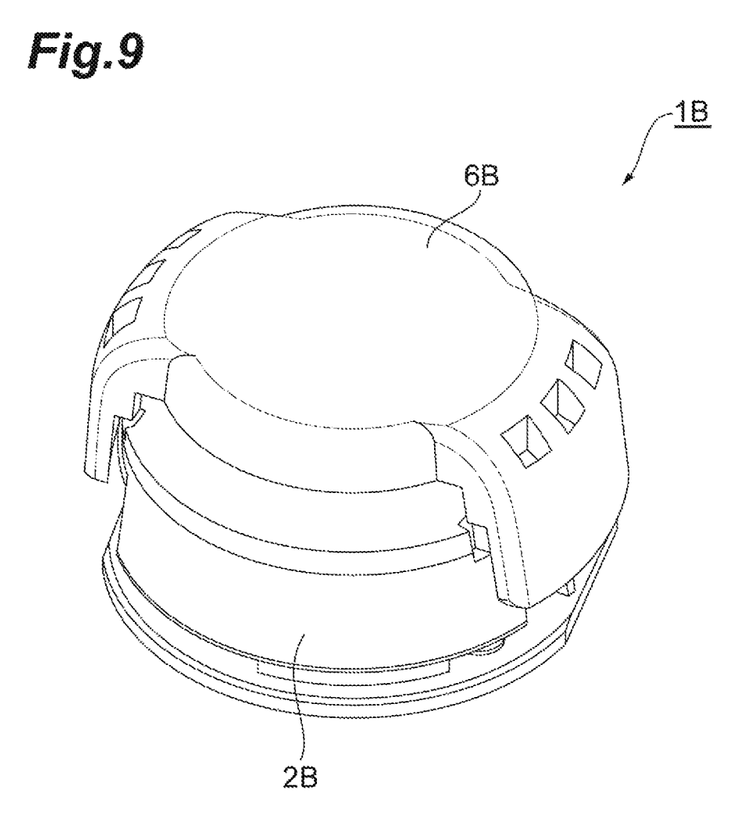
FIG. 9 is a perspective view illustrating an applicator according to the modification.

The external appearance (the overall shape) and the dimensions of the applicator are not limited to those described in the embodiment. An applicator 1B that is an example of an applicator with another external appearance and dimensions is illustrated FIG. 9. The structure of the applicator 1B is basically the same as that of the applicator 1. Mainly illustrated as the elements of the applicator 1B in FIG. 9 are a housing 2B corresponding to the housing 2 described above, and an actuation button 6B corresponding to the actuation button 6 or 6A described above. The external appearance and the dimensions of the applicator may be determined following any policy, while giving considerations to the ease of use, the dose of active components, the design, and the like.

REFERENCE SIGNS LIST 1, 1B . . . applicator, 2, 2B . . . housing, 2a, 2b . . . opening, 3 . . . coil spring, 4 . . . piston plate, 4d . . . hole, 5 . . . microneedle device, 6, 6B . . . actuation button, 11 . . . body, 11a . . . inner circumferential surface, 11b . . . outer circumferential surface, 11c . . . groove, 11d . . . clearance, 11e . . . stepped surface, 12 . . . lid, 21 . . . top plate, 21a . . . hole, 21e . . . central shaft, 22 . . . tubular portion, 22a . . . recessed portion, 22b . . . bulged portion, 22c . . . eave portion, 42 . . . bank, 42a . . . protruding portion, 42b . . . clearance, 43 . . . first protrusion, 44 . . . second protrusion, 61 . . . pressing portion, 62 . . . attaching portions, 63 . . . protruding portion, 64 . . . piston plate pushing portion, 64b . . . inclined surface, 65 . . . first engaging portion, 66 . . . second engaging portion, 66a . . . inclined surface, 66b . . . top surface, 67 . . . rim, C . . . central axis, P . . . biasing force, R . . . reactive force.

The invention claimed is:

1. An applicator for applying microneedles to skin, the applicator comprising:
   a housing having a tubular shape with one closed end, and configured to house an elastic member, and a piston plate for transmitting biasing force of the elastic member to the microneedles; and
   release means configured to release the piston plate engaged in a manner resisting against the biasing force of the elastic member in the housing, to cause the piston plate to move toward an opening of the housing along an axial direction of the housing, wherein
   the release means is configured, when the release means releases the engagement of the piston plate by moving toward the housing in the axial direction, to transmit force in a direction toward the opening of the housing, wherein
   the piston plate is provided with a hole, and
   the housing is provided with a protruding portion fitting inside the hole and protruding in the axial direction.

2. The applicator according to claim 1, wherein
the release means further comprises a release portion configured to release the engagement of the piston plate, and
the engagement of the piston plate is released by causing the release portion to rotate the piston plate when the release means moves in the axial direction.

3. The applicator according to claim 1, wherein
the release means includes an engaging portion, and
the engaging portion is configured to move in the axial direction and to become engaged with the housing when the release means releases the engagement of the piston plate.

4. The applicator according to claim 3, wherein
an eave portion is provided to an outer circumferential surface of the housing,
a locked condition and an unlocked condition are switched by the release means rotating in a circumferential direction of the housing,
the locked condition is a condition where the release means is prohibited from releasing the engagement of the piston plate,
the unlocked condition is a condition where the release means is permitted to release the engagement of the piston plate, and
the engaging portion is supported by the eave portion in the unlocked condition.

\* \* \* \* \*